US012529020B2

(12) United States Patent
Hingley et al.

(10) Patent No.: US 12,529,020 B2
(45) Date of Patent: Jan. 20, 2026

(54) SYSTEMS AND METHODS FOR ADHERING BIOFILM TO A LUMEN

(71) Applicant: Saban Ventures Pty Limited, Macquarie Park (AU)

(72) Inventors: Brian Hingley, Macquarie Park (AU); Ingeborg Kristina Palmer, Orange (AU); Joshua Storm Caley, Sydney (AU); Ashwin Gopalan Nair, Queensland (AU)

(73) Assignee: Saban Ventures Pty Limited, Macquarie Park (AU)

( * ) Notice: Subject to any disclaimer, the term of this patent is extended or adjusted under 35 U.S.C. 154(b) by 141 days.

(21) Appl. No.: 18/338,811

(22) Filed: Jun. 21, 2023

(65) Prior Publication Data

US 2023/0340381 A1 Oct. 26, 2023

Related U.S. Application Data

(63) Continuation of application No. 17/951,521, filed on Sep. 23, 2022, which is a continuation of application
(Continued)

(30) Foreign Application Priority Data

Dec. 11, 2017 (AU) ................................ 2017904967

(51) Int. Cl.
*C11D 3/382* (2006.01)
*A61B 1/12* (2006.01)
(Continued)

(52) U.S. Cl.
CPC ............ *C11D 17/003* (2013.01); *A61B 1/125* (2013.01); *B08B 3/08* (2013.01); *B08B 9/023* (2013.01);
(Continued)

(58) Field of Classification Search
CPC ....... C11D 3/2072; C11D 3/381; C11D 3/382; C11D 3/384; C11D 3/3845; B08B 3/08;
(Continued)

(56) References Cited

U.S. PATENT DOCUMENTS

| | | | |
|---|---|---|---|
| 5,669,945 | A | 9/1997 | Yam |
| 6,326,340 | B1 | 12/2001 | Labib et al. |

(Continued)

FOREIGN PATENT DOCUMENTS

| | | | |
|---|---|---|---|
| WO | 2004000475 | A1 | 12/2003 |
| WO | 2018064284 | A1 | 4/2018 |

OTHER PUBLICATIONS

Vickery et al, "The effect of multiple cycles of contamination, detergent washing, and disinfection on the development of biofilm in endoscope tubing", AM J Infect Control, 2009, pp. 470-475, vol. 37.*

(Continued)

*Primary Examiner* — Brian P Mruk
(74) *Attorney, Agent, or Firm* — Edell, Shapiro & Finnan, LLC

(57) ABSTRACT

A method of cleaning a contaminated surface, such as cleaning the elongate interior lumen of an endoscope contaminated with flesh, bone, blood, mucous, faeces or biofilm, said method comprising the steps of: providing a suspension of solid particles in a liquid to said contaminated surface, and flowing said suspension along said surface thereby to remove contaminant from the surface. The suspension is preferably a paste, where the solid material may be e.g. crystals of a salt, silicon oxide or organic material. The paste preferably has a solid fraction between 5 and 55%. A rheology modifier may be present.

33 Claims, 3 Drawing Sheets

Related U.S. Application Data

No. 16/771,817, filed as application No. PCT/AU2018/051308 on Dec. 6, 2018, now Pat. No. 11,453,846.

(51) Int. Cl.

| | |
|---|---|
| ***A61B 90/70*** | (2016.01) |
| ***A61L 2/02*** | (2006.01) |
| ***A61L 2/18*** | (2006.01) |
| ***B08B 3/08*** | (2006.01) |
| ***B08B 9/023*** | (2006.01) |
| ***B08B 9/032*** | (2006.01) |
| ***C11D 3/384*** | (2006.01) |
| ***C11D 7/12*** | (2006.01) |
| ***C11D 7/20*** | (2006.01) |
| ***C11D 7/26*** | (2006.01) |
| ***C11D 7/50*** | (2006.01) |
| ***C11D 17/00*** | (2006.01) |
| ***G01N 11/04*** | (2006.01) |

(52) U.S. Cl.

CPC .............. *B08B 9/0326* (2013.01); *C11D 7/12* (2013.01); *C11D 7/20* (2013.01); *C11D 7/265* (2013.01); *C11D 7/5022* (2013.01); *B08B 2209/032* (2013.01); *C11D 2111/14* (2024.01)

(58) Field of Classification Search

CPC ......... B08B 9/023; B08B 9/032; G01N 11/04; A61B 1/12; A61B 1/125; A61B 90/70; A61L 2/02; A61L 2/18

See application file for complete search history.

(56) References Cited

U.S. PATENT DOCUMENTS

| | | | |
|---|---|---|---|
| 6,454,871 | B1 | 9/2002 | Labib et al. |
| 6,475,434 | B1 * | 11/2002 | Darouiche .............. A61L 31/08 422/35 |
| 6,503,875 | B1 | 1/2003 | Olson et al. |
| 7,435,426 | B2 | 10/2008 | Einziger et al. |
| 2003/0121532 | A1 | 7/2003 | Coughlin et al. |
| 2003/0221707 | A1 | 12/2003 | Blanton et al. |
| 2004/0002438 | A1 | 1/2004 | Hawkins et al. |
| 2005/0161372 | A1 | 7/2005 | Colic |
| 2012/0066851 | A1 | 3/2012 | Gonzales et al. |
| 2012/0071379 | A1 | 3/2012 | Gonzales et al. |
| 2012/0281214 | A1 | 11/2012 | Scheuren |
| 2014/0105831 | A1 | 4/2014 | Gonzales et al. |
| 2015/0007400 | A1 | 1/2015 | Gonzales et al. |
| 2016/0081756 | A1 | 3/2016 | Sommacal |
| 2016/0220098 | A1 | 8/2016 | Bancroft et al. |
| 2018/0007914 | A1 | 1/2018 | Sanford et al. |
| 2018/0094214 | A1 | 4/2018 | Labib et al. |
| 2021/0068643 | A1 | 3/2021 | Spargo et al. |
| 2021/0189300 | A1 | 6/2021 | Spargo et al. |

OTHER PUBLICATIONS

International Search Report and Written Opinion Issued Feb. 13, 2019 in PCT/AU2018/051308, 13 pages.

European Search Report, Application No. 18889551.0, dated Jul. 26, 2021, 8 pages.

Michelle J. Alfa et al., "A novel polytetrafluoroethylene-channel model, which simulates low levels of culturable bacteria in buildup biofilm after repeated endoscope reprocessing," Gastrointestinal Endoscopy, 2017, 442-451.e1, vol. 86, No. 3, http://dx.doi.org/10.1016/j.gie.2017.05.014.

Michelle J. Alfa et al., "Sterile Reverse Osmosis Water Combined with Friction are Optimal for Channel and Lever Cavity Sample Collection of Flexible Duodenoscopes," Frontiers in Medicine, Nov. 2017, 4:191, doi: 10.3389/fmed.2017.00191.

Michelle J. Alfa et al., "Simulated-Use Polytetrafluorethylene Biofilm Model: Repeated Rounds of Complete Reprocessing Lead to Accumulation of Organic Debris and Viable Bacteria," Infection Control & Hospital Epidemiology, Nov. 2017, 1284-1290, vol. 38, No. 11, DOI: 10.1017/ice.2017.215.

Cristiana da Costa Luciano et al., "A new buildup biofilm model that mimics accumulation of material in flexible endoscope channels," Journal of Microbiological Methods, 2016, 224-229, vol. 127, http://dx.doi.org/10.1016/j.mimet.2016.06.022.

Michelle J. Alfa et al., "Modeling microbial survival in buildup biofilm for complex medical devices," BMC Infectious Diseases, May 2009, 9:56, doi:10.1186/1471-2334-9-56.

Karen Vickery et al., "The effect of multiple cycles of contamination, detergent washing, and disinfection on the development of biofilm in endoscope tubing," Am J Infect Control, 2009, 470-475, vol. 37, doi:10.1016/j.ajic.2008.09.016.

* cited by examiner

SYSTEMS AND METHODS FOR ADHERING BIOFILM TO A LUMEN

REFERENCE TO RELATED APPLICATIONS

This application is a continuation of U.S. application Ser. No. 17/951,521, filed Sep. 23, 2023, which is a continuation of U.S. application Ser. No. 16/771,817, filed Jun. 11, 2020, now U.S. Pat. No. 11,453,846, which is the 371 National Stage Application of International Application No. PCT/AU2018/051308, filed Dec. 6, 2018, which claims priority to Australia Patent Application No. 2017904967, filed Dec. 11, 2017, the entire contents of which are incorporated herein by reference.

TECHNICAL FIELD

This invention relates to methods for cleaning the interior cavities and lumens of devices, and in particular for cleaning the lumens of contaminated medical instruments.

The invention has been developed primarily for use in the cleaning the interior lumens of endoscopes and will be described hereinafter to reference to this application. However, it will be appreciated that the invention is not limited to this particular field of use.

BACKGROUND ART

An endoscope is an elongate tubular instrument that may be rigid or flexible and which incorporates an optical or video system and light source. Typically, an endoscope is configured so that one end can be inserted into the body of a patient via a surgical incision or via one of the natural openings of the body. Internal structures near the inserted end of the endoscope can be thus be viewed by an external observer.

As well as being used for investigation, endoscopes are also used to carry out diagnostic and surgical procedures. Endoscopic procedures are increasingly popular as their minimally invasive nature provides a better patient outcome (through reduced healing time and exposure to infection) and also enables hospitals and clinics to achieve higher patient turnover.

Endoscopes typically take the form of a long tube-like structure with a 'distal tip' at one end for insertion into a patient and a 'connector end' at the other with a control handle at the centre of the length. Typically, the connector end is hooked up to a supply of light, water, suction and pressurised air. The control handle is held by the operator during the procedure to control the endoscope via valves and control wheels. The distal tip contains the camera lens, lighting, nozzle exits for air and water, exit point for suction and forceps.

All endoscopes have internal channels used either for delivering air and/or water, providing suction or allowing access for forceps and other medical equipment required during the procedure. Some of these channels run from one end of the endoscope to the other while others run via valve sockets at the control handle. Some channels bifurcate while and others join from two into one.

Endoscopes used for diagnostic or surgical purposes contain a long, narrow lumen (sometimes referred to as a forceps channel) through which surgical apparatus can pass. The apparatus can be used to remove diseased tissue or collect tissue samples for diagnosis. The collected tissue is then removed from the endoscope by drawing it outwards through the lumen. As a consequence, the lumen can become contaminated with traces of tissue from the patient. Blood, mucus and faecal matter can also readily find their way into the lumen.

The high cost of endoscopes means they must be re-used. Because of the need to avoid cross infection from one patient to the next, each endoscope must be thoroughly cleaned and disinfected or sterilised after each use. This involves the cleaning of not only the outer skin of the endoscope, but also cleaning and disinfecting the lumen. Endoscopes used for colonoscopic procedures are approximately two meters long and have one or more lumen channels of diameter no more than a few (2-4) millimetres. Ensuring that such long narrow channels are properly cleaned and disinfected between patients presents a considerable challenge.

The challenge of cleaning is also made more difficult by the fact that there is not just one configuration for endoscopes. There are a variety of endoscopic devices suited to the particular cavity to be investigated i.e. colonoscopes inserted into the colon, bronchoscopes inserted into the airways, gastroscopes for investigation of the stomach. Gastroscopes, for instance, are smaller in diameter than colonoscopes, bronchoscopes are smaller again and shorter in length, while duodenoscopes have a different tip design to access the bile duct, and so on.

Some endoscopes, such as duodenoscopes, also possess a "blind lumen", closed at one end which can be even more difficult to clean.

A variety of options are available to mechanically remove biological residues from the lumen, which is the first stage in the cleaning and disinfection process. By far the most common procedure for cleaning the lumens using small brushes mounted on long, thin, flexible lines. Brushing is the mandated means of cleaning the lumen in some countries.

These brushes are fed into the lumens while the endoscope is submerged in warm water and a cleaning solution. The brushes are then pushed/pulled through the length of the lumens in an effort to scrub off the soil/bio burden. Manual back and forth scrubbing is required. Water and cleaning solution is then flushed down the lumens. These flush-brush processes are repeated three times or until the endoscope reprocessing technician is satisfied that the lumen is clean. At the end of this cleaning process air is pumped down the lumens to dry them.

A flexible pull-through having wiping blades may also be used to physically remove material. A liquid flow through the lumen at limited pressure can also be used.

In general, only the larger suction/biopsy lumens can be cleaned by brushing or pull throughs. Air/water channels are too small for brushes so these lumens are usually only flushed with water and cleaning solution.

After mechanical cleaning, a chemical clean is carried out to remove the remaining biological contaminants. Because endoscopes are sensitive and expensive apparatus, the biological residues cannot be treated at high temperatures or with strong chemicals. For this reason, the mechanical cleaning needs to be as thorough as possible.

In many cases, the current mechanical cleaning methodologies fail to fully remove biofilm from lumens, particularly where cleaning relies on liquid flow alone.

Regardless of how good the conventional cleaning processes are, it is almost inevitable that a small microbial load will remain in the channel of the lumen. There has been significant research to show that the method of cleaning with brushes, even when performed as prescribed, does not completely remove biofilm in endoscope lumens.

As well as lacking in efficacy, the current manual brushing procedures suffer from other drawbacks.

The large number of different endoscope manufacturers and models results in many minor variations of the manual cleaning procedure. This has led to confusion and ultimately poor compliance in cleaning processes.

The current system of brushing is also hazardous to the endoscope reprocessing staff who clean them. Brushing can disperse small particles or aerosols of bioburden into the air which can be accidentally ingested or inhaled. The chemicals that are currently used to clean endoscopes can adversely affect the reprocessing staff.

The current system of manual brushing is also labour intensive, leading to increased cost.

Thus, the current approaches to cleaning and disinfecting the lumens in medical apparatus are still inadequate and residual microorganisms are now recognised as a significant threat to patients and staff exposed to these devices. There is evidence of bacterial transmission between patients from inadequate cleaning and disinfection of internal structures of endoscopes which in turn has led to patients acquiring mortal infections. Between 2010 and 2015 more than 41 hospitals worldwide, most in the U.S., reported bacterial infections linked to the scopes, affecting 300 to 350 patients (http://www.modernhealthcare.com/article/20160415/NEWS/160419937)

It would be expected that a reduction in the bioburden in various medical devices would produce a concomitant overall reduction in infection rates and mortality.

In addition, if endoscopes are not properly cleaned and dried, biofilm can build up on the lumen wall.

If an endoscope is not properly cleaned and dried, biofilm can form on the interior surfaces of the device. Biofilms start to form when a free-floating microorganism attaches itself to a surface and surrounds itself with a protective polysaccharide layer. The microorganism then multiplies, or begins to form aggregates with other microorganisms, increasing the extent of the polysaccharide layer. Multiple sites of attachment can in time join up, forming significant deposits of biofilm.

Once bacteria or other microorganisms are incorporated in a biofilm, they become significantly more resistant to chemical and mechanical cleaning than they would be in their free-floating state. The organisms themselves are not inherently more resistant, rather, resistance is conferred by the polysaccharide film and the fact that microorganisms can be deeply embedded in the film and isolated from any chemical interaction. Any residual biofilm remaining after an attempt at cleaning quickly returns to an equilibrium state and further growth of microorganisms within the film continues.

Endoscopes lumens are particularly prone to biofilm formation. They are exposed to significant amounts of bioburden, and subsequent cleaning of the long narrow lumens is quite difficult due to inaccessibility and the inability to monitor the cleaning process. There is considerable pressure in medical facilities to reprocess endoscopes as quickly as possible. Because endoscopes are cleaned by hand, the training and attitude of the technician are important in determining the cleanliness of the device.

Residual biofilm on instruments can result in a patient acquiring an endoscope acquired infection. Typically, these infections occur as outbreaks and can have fatal consequences for patients.

It is an object of the present invention to overcome or ameliorate at least one of the disadvantages of the prior art, or to provide a useful alternative.

Any discussion of the prior art throughout the specification should in no way be considered as an admission that such prior art is widely known or forms part of common general knowledge in the field.

SUMMARY OF THE INVENTION

According to a first aspect the invention provides a method of cleaning a contaminated surface, said method comprising the steps of: providing a suspension of solid particles in a liquid to said contaminated surface, and flowing said suspension along said surface thereby to remove contaminant from the surface.

The contaminated surface is, for example, the surface of a medical instrument which may be the interior surface of a medical instrument, such as endoscope. More particularly, the interior surface is an elongate lumen.

The contaminant may, for example, be flesh, bone, blood, mucous, faeces or biofilm.

The suspension may be flowed continuously in a single direction, or pulsed or the suspension may be flowed alternately in different directions.

The flow rate used is normally the maximum allowable as determined by the pressure rating of the instrument.

The method may also further include a rinsing step.

In one embodiment, the suspension is a paste. The solid particles are preferably salt crystals, for instance, crystals of sodium bicarbonate, potassium bicarbonate, sodium phosphate, potassium phosphate, sodium nitrate, potassium nitrate, sodium benzoate, potassium benzoate, borax or other abrasive particles such as calcium carbonate, silicates or mixtures thereof.

The term "paste" as used herein is a mixture of solid particles suspended in a fluid which will behave largely as a solid (although one which is plastic in nature and may exhibit slumping) until a sufficiently large load or stress is applied, at which point it flows like a fluid. In rheological terms, a paste is an example of a Bingham plastic fluid.

In the case of a paste, any solid fraction that serves to provide cleaning may be used, for example, any solid content between 1 and 99% by weight. The solid fraction is preferably 5 and 55%, 30 and 55%, 35 and 50% or between 40 and 45%.

The liquid is selected so as not to dissolve the abrasive particles. The liquid may be a saturated solution of a salt, or a water/alcohol mixture, water glycol mixture or water glycerol mixture.

The paste may further include a rheology modifier to change one or more properties such as viscosity or yield point, or to impart to the suspension other non-Newtonian properties. The rheology modifier may be for example, xanthan gum.

In one embodiment, a useful paste comprises about ⅓ sodium benzoate, ⅓ sodium bicarbonate and ⅓ water.

In one embodiment, the paste comprises by weight 25-45% sodium benzoate. In another embodiment, the paste comprises by weight 25-45% sodium bicarbonate. In another embodiment the paste comprises by weight 25-45% water.

In a preferred embodiment, the the paste comprises by weight 25-45% sodium benzoate, 25-45% sodium bicarbonate and 25-45% water. A particularly suitable paste comprises by weight sodium benzoate, sodium bicarbonate and water in the respective ratios 27:35:38 w/w.

In another embodiment of the present invention, the paste cleaning is followed by a chemical or enzymatic clean to complement the physical cleaning of the paste. The chemical or enzymatic cleaning may be conducted immediately following on from the paste cleaning, or may involve intermediate rinsing. Additional rinsing and/or drying steps may be carried out as necessary.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The term "cleaning" as used herein is intended to refer to the removal of inorganic and organic matter, including but not limited to bio burden, microorganisms, biofilm and other foreign objects such as surgical clips.

DESCRIPTION OF THE INVENTION

Figure 1:
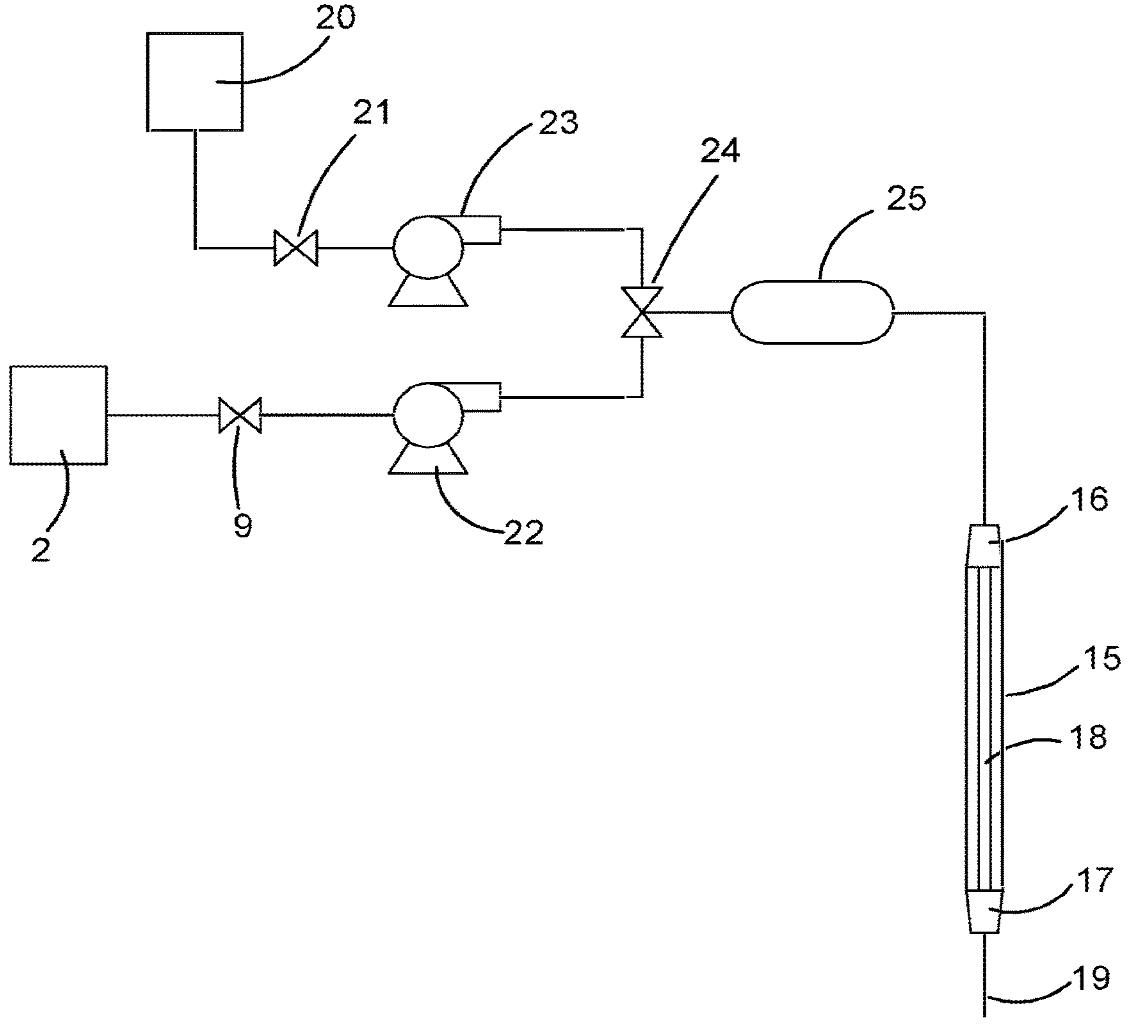
FIG. 1 shows a suspension or paste cleaning prototype.

The present invention in it broadest form relates to passing a suspension of solid particles in a liquid through the lumen of an endoscope for the purposes of mechanically cleaning the endoscope channel of bioburden, which includes residual tissue such as flesh, bone, blood, mucous and faeces remaining after diagnostic or surgical procedures. The present invention also relates to the use of suspensions to remove biofilm.

The invention will be described with reference to the use of a flowable, conveyable paste for lumen cleaning. Based on the teaching of the present invention it will be understood by those skilled in the art of that the invention may be embodied in other forms and may utilise other liquids and other particles in the cleaning of endoscope lumens and other instruments without departing from the concepts herein described.

For instance, the methods of the present invention are useful in cleaning other lines susceptible to contamination. Particularly, the methods of the present invention are useful in cleaning water lines, such as those used in the food, beverage, manufacturing or airconditioning industries. Such lines are very susceptible to biofilm contamination.

In an embodiment the suspension comprises solid particles in a carrier fluid in the form of a paste. The carrier fluid is selected to not dissolve, or to only provide minimal dissolution, of the solid particles, and to provide a suitably stable suspension of the solid particles. Suitable carrier fluids include water/alcohol mixtures, water glycol mixtures or water glycerol mixtures. If the solid particles are a water-soluble salt, then a saturated aqueous solution of the water-soluble salt can be used as a carrier.

The invention using pastes is described with reference to specific examples, however, it will be appreciated by those skilled in the art that the process is, in very large part, a physical process rather than a chemical process, so the exact chemical nature of the components is not critical, but rather, the resultant physical properties of the mixture that arise from the interrelationship of the components. The physical properties of the mixture that are believed to give rise to the desirable cleaning effect include: the paste yield stress; the viscosity in the range of shear rates that are present when cleaning; if viscoelastic properties are present, then by how much; the rate of any shear thinning or thickening properties.

The nature of the particles, including crystal size and morphology, have also been shown to contribute to the cleaning effect.

The solid particles may be for example salt crystals. Suitable types of salt crystals include, but are not limited to, sodium bicarbonate, potassium bicarbonate, sodium phosphate, potassium phosphate, sodium nitrate, potassium nitrate, sodium benzoate, potassium benzoate, borax, calcium carbonate or mixtures thereof.

Again, the density, size and morphology of the salt crystals can be selected for optimal cleaning.

The invention will be described with reference to the conveyable paste being conveyed by pumping (i.e. pushed) but a conveyable paste may equally be conveyed by way of reduced pressure or suction (i.e. pulled).

Preliminary studies indicate that particles that are too large are difficult to pump and do not provide sufficient granularity to evenly scour the entire tube wall, whereas particles that are too small tend to exhibit more fluid like properties, rather than the necessary solid abrasion required. Particles will ideally be within the range of 1 to 250 microns, and more particularly, 10 to 50 microns.

In addition to salts, other particles, such as hard plastic objects, silica, ceramics etc. can be used as the suspended solid, although caution needs to be exercised as the use of excessively hard particles may damage the endoscope lumen.

When a paste is used, the solid fraction is between 30 and 70% w/w, more particularly between 30 and 50% w/w and even more particularly between 40 and 50% w/w.

The paste needs to be flowable and it is desirable to have a viscosity that allows good flowability in combination with suitable abrasive properties. 50,000 to 100,000 cP (centipoise) at ambient temperatures (similar to toothpaste) is a suitable viscosity. If necessary, rheology modifiers, such as polyvinyl alcohol, polymers or gums can be added to change the rheological profile of the paste, such as by increasing viscosity, and assist in the formation of a stable system.

One particularly useful paste has been found to be that made from ⅓ sodium benzoate, ⅓ sodium bicarbonate and ⅓ water by weight. Sodium benzoate has a solubility of around 50 g/100 mL in water and sodium bicarbonate has around 6.9 g/100 mL. The water thus becomes a saturated salt solution as carrier fluid. A significant residual solid component of each of the bicarbonate and benzoate crystals remains present to produce a suitable paste.

In one embodiment, the paste is premixed and provided contained in a cartridge. The cartridge containing the premixed paste is placed in line with the endoscope lumen and simply pumped through the lumen under pressure. This embodiment is shown in FIG. 2.

Figure 2:
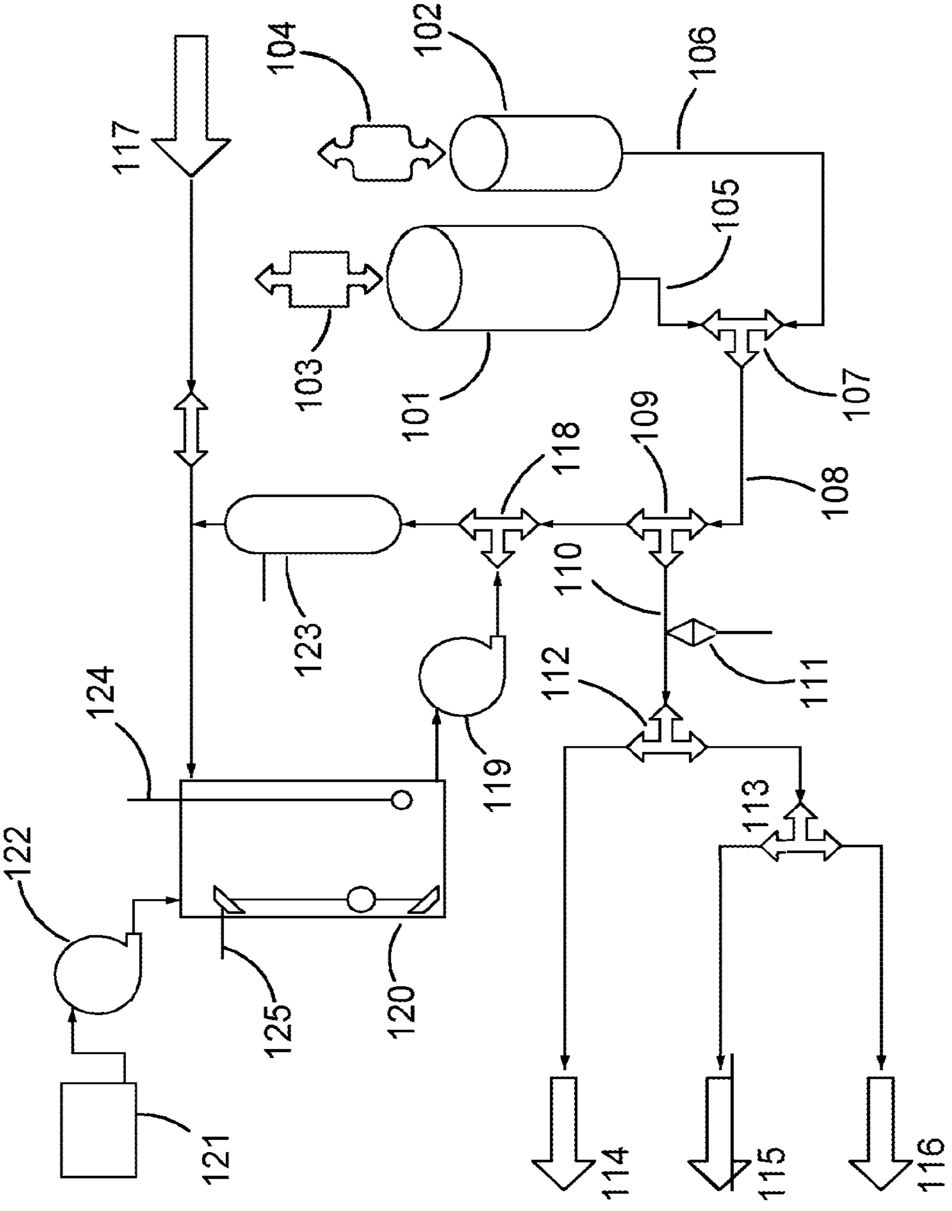
FIG. 2 shows an alternate suspension or paste cleaning prototype.

The embodiment in FIG. 2 shows apparatus which contains two separate cartridges, a thick (relatively viscous) paste cartridge, 101 and a thin (relatively non-viscous) paste cartridge 102. The paste is forced from the cartridges by engagement with plungers or similar driven by respective linear drives 103 and 104. Paste from each cartridge flows under pressure down line 105 and 106 respectively, to valve 107. Valve 107 allows for the selection and/or mixing of the thick paste from 101 or the thin paste from 102 as desired.

The selected paste or selected paste mixture flows down line 108 to valve 109 and through line 110, where the pressure is sensed by pressure sensor 111. The pressure sensor ensures that the paste flows at an optimal speed, i.e., as fast as practicable without approaching too closely the pressure limit of the endoscope lumen. The pressure sensor can be connected to a feedback or control mechanism to shut off the linear drives should the pressure begin to approach levels that may damage the endoscope.

The valves 112 and 113 can be maintained in configurations as to control the flow of the paste through the various channels 114, 115 and 116 (suction/biopsy, air/water, forward water jet etc.) of the endoscope as desired.

The apparatus in disclosed FIG. 2 is also configured to provide a wash with water, an enzyme cleaner or other detergent after the physical clean of the paste has been completed. When the paste cleaning is finished, valve 109 is closed to the flow of any paste or paste mixture, but is opened to be in fluid communication with valve 118. Valve 118 is in turn in fluid communication with diaphragm pump 119 which, pumps a ready to use aqueous solution of enzyme from tank 120 along the lines to endoscope channels 114, 115 and/or 116 as desired. The pressure sensor 111 in this case can be used to ensure the aqueous enzyme solution is not pumped through the endoscope channels at excessive pressures.

The paste flows down the desired lumen channels of the endoscope and may be discharged via an exit line into a drain.

The concentration of enzyme solution in tank 120 can be regulated by controlling the addition of enzyme from enzyme concentrate reservoir 121 by peristaltic pump 122 and water, through water inlet 117. The temperature of the enzyme system can be independently optimised by the inclusion of a heating circuit that includes the tank 120 and an-in line heater 123. The aqueous enzyme solution can be cycled through the heater until the desired temperature in tank 120 is achieved. A thermocouple 124 ensures that the ready to use enzyme cleaner in tank 120 is maintained at optimal active temperature before use. Float switch 125 ensures the liquid level in the reservoir tank is maintained within the proper operational limits.

The aqueous enzyme solution passes through the channels of the endoscope and may be discharged via an exit line into a drain.

It will also be seen that by selection of the various valve positions that water from inlet 117 can be passed via line 110, where it can be used at a measure pressure to rinse residual cleaning paste or aqueous enzyme.

The paste is pumped down the lumens at the maximum pressure permissible by the endoscope manufacturer. A typical maximum allowable air or water pressure for aerating or irrigating endoscope channels is 0.5 MPa (5 kgf/cm$^2$, 71 psig). At this pressure, the flow rate for the paste is less than 10 cm/s, which is considerably less than the flow rate of water used to flush the channel.

After passing through the lumen, the paste is discharged into a drain along with the dislodged contaminants. The paste can be further diluted with water to remove soluble components and allow any insoluble or precipitated components to be isolated, for example, by filtration or centrifugation, which can also allow capture of removed residual material dislodged from the lumen. The residual material can be removed and treated as biological waste. The other residues can be further sterilised if desired and discharged as necessary.

In one embodiment, the paste may be made to flow in a single direction at a constant rate. Alternatively, the flow may be pulsed, that is, the paste moves, rests for a period and then continues to move in the same direction, with that being repeated. Alternatively, in another embodiment, the flow of the paste at times is intermittently reversed, creating a back and forth scrubbing motion of the solid particles which aids in removing any residual bioburden or biofilm that may have been flattened in a particular direction by the flow of the paste in the primary direction (from the reservoir towards the discharge point of the endoscope). In yet a further embodiment, the flow may be fed through the endoscope in a manner interspersed with one or more other liquid, gas or paste flows. For instance, a chemical clean may be included between paste flow phases to assist in the removal of residues.

The paste is passed through the endoscope for a suitable time to remove the biological material, depending upon the initial level of contamination and the construction of the endoscope. Once the paste cleaning has finished, the lumen of the endoscope can be flushed with water and air dried, or dried in any other suitable manner.

The paste may also contain chemicals to alter its characteristics. For example, non-solvents for the salt, such as alcohols and glycols may be used. Other agents, such as surfactants, disinfectants, residual treatments etc. may also be added to the paste for beneficial effect. If used, these can be added through either tank 2 or 20, or via another tank directly into the mixing ratio valve 24.

Of course, in the present invention, slurries of insoluble materials, such as polymer or silaceous particles may be used. Although these would be expected to show similar beneficial effects, they do suffer from the drawback that the solids cannot be readily dissolved, a factor which in the case of the present invention assists greatly in their removal in subsequent rinsing, disinfection and drying steps, as well as facilitating their disposal.

Experimental

1. Test Soils and Contaminants

The removal of bioburden from endoscope lumens was modelled using a variety of standard and customised test soils applied to the inner surfaces of teflon or other suitable tubing in order to mimic the inner lumens of endoscopes. The soils were pumped into the tube or manually applied to the inner surfaces of the tubes and allowed to dry or bake onto the surface as required. In addition to modelling soils, the present inventors also employed standardised protocols for biofilm for testing and residual protein.

The procedures for soil preparation, as well as the fixed protein and biofilm contaminations are as follows:

A. Soil 5B (Pumped Soil)

Soil 5B is a standardised pumped test soil for use in experiments in the cleaning of medical devices.

Ingredients:

3 g hog mucin
5 ml horse blood
1.5 ml deionised water
50 ml egg yolk 3.0 g of mucin was mixed with 5 mL of horse blood and stirred until smooth, 1.5 mL of deionised water was added and the mixture again fully stirred. 5×10 mL batches of egg yolk were added to the mixture while stirring. The mixture was stored in a cool dry environment in a closed container.

Teflon tubes (ID 4.25 mm, OD 5.1 mm, 10 cm long) were inoculated by pumping the soil into the tube with a syringe, holding the soil in position for 5 seconds and then pumping the soil back into the syringe.

The inoculated tubes were fixed in place inside a small container. The container was then placed on top of a rotational mixing apparatus situated inside an incubator. The tubes were rotated at medium speed in the incubator for 30 minutes at 40° C. The tubes were then connected to a 4-port air pump machine (eight tubes at a time via four T-Pieces)

within the 40° C. incubator. The tubes were held in the incubator for a further 15 minutes at low airflow. Any tubes that leaked during the airflow stage were discarded. The tubes were stored in a cool dry environment.

B. Soil 5D (Brushed Soil)

Soil 5D is a standardised brushed test soil for use in experiments in the cleaning of medical devices.

Ingredients:

3 g hog mucin
5 ml horse blood
1.5 ml deionised water
50 ml egg yolk 3.0 g of mucin was mixed with 5 mL of horse blood and stirred until smooth, 1.5 mL of deionised water was added and the mixture again fully stirred. 5×10 mL batches of egg yolk were added to the mixture while stirring. The mixture was stored in a cool dry environment in a closed container.

Teflon tubes (ID 4.25 mm, OD 5.1 mm, 10 cm long) were inoculated one at a time. A small brush was dipped into the soil and then passed through the inside of the tube several times from each direction until an even coating is achieved. The brush was removed along with any soil that builds up around the ends of the tube and any that is on the exterior of the tube.

For the purposes of the present invention, soil was applied to attain a target weight of between 0.0685 g and 0.0925 g.

The inoculated tubes were placed in an incubating oven for 5 minutes at 40° C. Advantageously, the tubes were used immediately. If necessary, the tubes could be stored during down time in testing in a zip-lock bag with as much air removed as possible.

C. ATS2015

ATS2015 is a commercially available artificial test soil used as to model, available from Healthmark Industries Co. It contains haemoglobin, protein, carbohydrate lipids and insoluble fibres and is used as a standardized test soil in proportion found on clinically used medical devices, including specifically flexible endoscopes.

Ingredients:

ATS2015 dry powder—0.0905 g per mL final volume
Defibrinated blood (sheep)—0.2 mL per mL final volume
Sterile water—1 mL per mL final volume Water was added to the ATS 2015 dry powder and vortexed/shaken for 10 minutes or until completely mixed. The foam was allowed to settle for 20 minutes. The blood was added and mixed gently.

When preparing ATS2015 soil for biological testing, a microbe containing suspension was added after the dry powder had been dissolved. The amount of water used to introduce the microbe suspension was noted in advance, so the final volume of sterile water was still only 1 mL The reconstituted mixture could be satisfactorily stored in an air-tight container at 2-5° C., away from light and heat for up to two weeks.

Soil was pumped into Teflon tubes (ID 4.25 mm, OD 5.1 mm, 10 cm long) using a syringe. The tube was completely filled soil. The tubes were held vertically to allow draining, with a small volume of air applied to the top of the syringe at the completion of the draining process. The inoculated tubes were allowed to dry on a bench at room temperature (15-25° C.) for 1 hour. Cleaning tests were conducted within 1 hour of preparation.

D. Black Soil

Black soil is a standard test soil described in ISO/TS 15883-5:2005(E) useful in experiments relating to the cleaning of medical devices.

Ingredients:

30 g unbleached plain wheat flour
15 g water soluble wallpaper adhesive powder
1 hens egg (60-65 g)
10 ml black ink (water tolerant/permanent, Indian ink)
240 ml water The ingredients above were mixed together to form a uniform thick paste. The paste could be used immediately or stored in an air-tight container at 2-5° C. for up to one month.

Black soil at room temperature was pumped into Teflon tubes (ID 4.25 mm, OD 5.1 mm, 10 cm long) via a syringe. The syringe plunger was rapidly withdrawn to extract excess soil such that there was a thick, uniform coating of soil on the inside of the lumen with an unbroken air-path from one end of the tube to the other. Unsuitable tubes were refilled or discarded. The inoculated tubes were allowed to dry on a bench at room temperature (15-25° C.) for 30-35 minutes and used within a subsequent 30 minute period.

E. Edinburgh Soil

Edinburgh soil is a standard test soil described in ISO/TS 15883-5:2005(E) for use in experiments in the cleaning of medical devices.

Ingredients:

100 ml fresh egg yolk
10 ml defibrinated blood (horse or sheep)
2 g dehydrated hog mucin The above ingredients were mixed together to give a liquid of uniform consistency. The liquid was used immediately or stored in an air-tight container at 2-5° C. for up to a week.

Soil at room temperature was pumped into Teflon tubes (ID 4.25 mm, OD 5.1 mm, 10 cm long) via a syringe. The tubes were held vertically to allow excess soil to drain. The last traces of bulk soil were removed using a syringe to push a small amount of air through the tube. The inoculated tubes were allowed to dry on a bench at room temperature (15-25° C.) for between 30 and 120 minutes.

F. Fixed Protein

Ingredients:

1% glutaraldehyde
1% horse serum

Equipment:

1% horse serum was pumped through a Teflon tubes (ID 4.25 mm, OD 5.1 mm). The volume used was 2×tube volumes. After 20 minutes, 2×tube volumes of 1% glutaraldehyde was pumped through the tube. After 10 minutes, the process was repeated. Altogether, there were five cycles of horse serum followed by five cycles of glutaraldehyde. The tube was then washed with 10 tube volumes.

The tube was stained for protein as disclosed below, and could be cut into 10 cm lengths.

G. Biofilm

This procedure outlines the preparation and growth of biofilm of *Pseudomonas aeruginosa* ATCC15442 in tubes for use in experiments in the cleaning of medical devices.

*Pseudomonas aeruginosa* ATCC15442 culture was grown overnight in Synthetic Broth+Glucose (5 mL) at 37° C. The microbial inoculant concentration was determined by % transmission by spectrophotometry at 580 nm wavelength. The level of inoculum was also determined by historical data.

All apparatus were sterilised before use and the conditions used were aseptic. Teflon tubes (ID 4.25 mm, OD 5.1 mm, up to 5 metres long) used for inoculation were sterilized in an autoclave.

5% TSB (tryptic soy broth, equates to 50 mL/L) in 1 L of sterile distilled water was inoculated with ~0.2% of *P.*

*aeruginosa* isolated culture. The exact volume of microorganism added was dependent on the % Transmission). The inoculated growth medium was placed into a 1 L Schott bottle, which was stirred.

Figure 3:
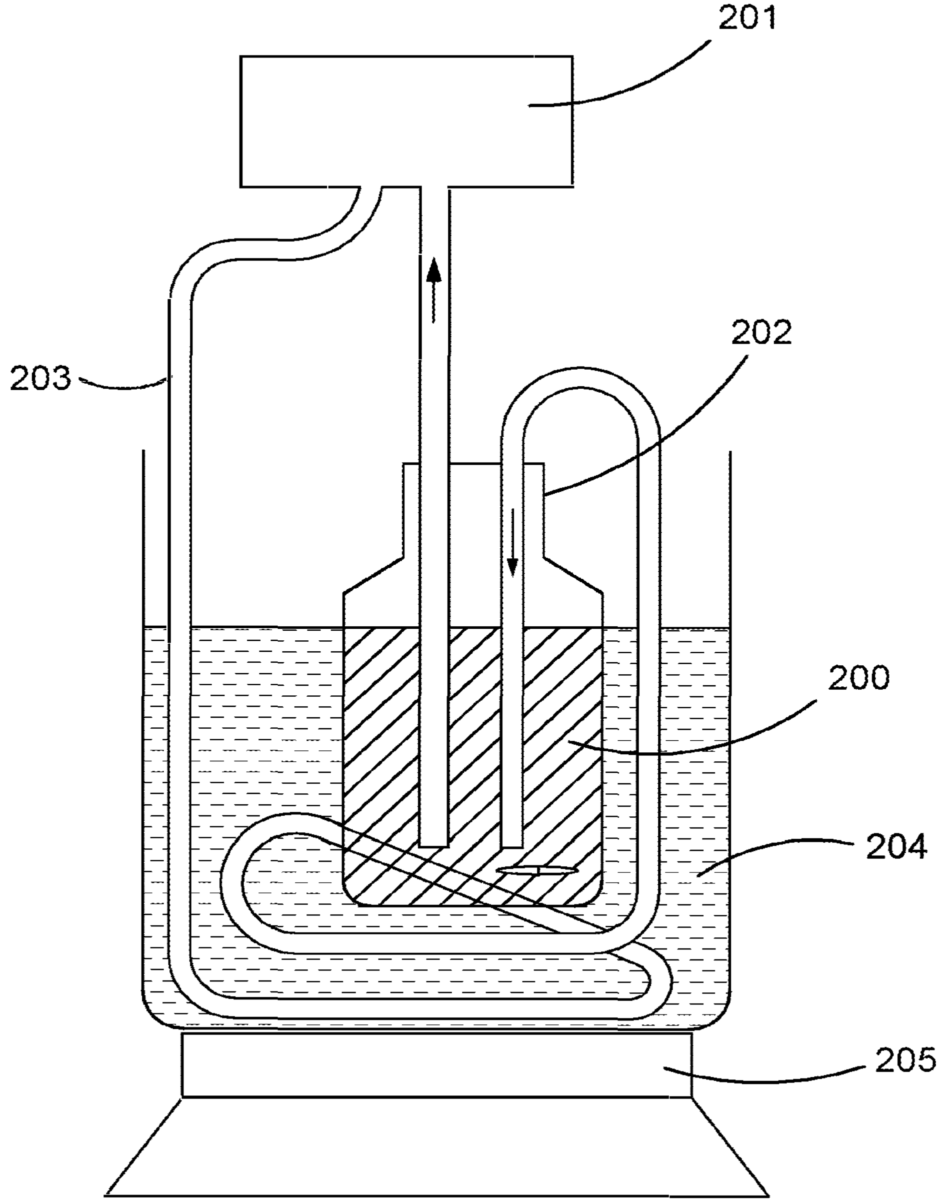
FIG. 3 is shows an arrangement used to produce standardised biofilm deposits in a lumen.

The setup, which shows the water cycling in the closed system immersed in the waterbath, is shown in FIG. 3

The inoculated media 200 was then pumped via pump 201 at the lowest available flow setting (~5 L/min) such that the growth media was transferred from the Schott flask 202, through teflon tube 203 to be inoculated and then back into the Schott flask. The Schott flask 202 and teflon tube 203 were immersed in a water bath 204 at 30° C., such that the inoculated grown medium was contained below the level of the water bath and always maintained at 30° C. by heater 205. The apparatus was checked to ensure that there were no bubbles in the teflon tubing and that the inoculated grown medium was in contact with every part of the internal of the tube as it flowed through.

Growth Cycle:

After 48 hours, the pump was stopped and the growth medium was allowed to empty from the tube at a slow rate. The growth medium was replaced, the tube refilled and the pump restarted After a further 72 hours, the tube was again drained and the growth medium replaced. The pump was restarted and allowed to run for a further 48 hours, after which the tubing was removed and drained and was ready for testing. The inoculated tubing could be stored overnight at −4° C. The tubing could be cut to desired lengths and tested.

2. BioBurden Test Protocols

Testing for the presence of residual bioburden in the enclosed parts of medical instruments is challenging. In consequence, there is little available in the way of established protocols for assessing either the quantity or the activity of biological residue. The Applicant has developed the following tests which enable rapid and reproducible quantification of biological residues.

2.1. Procedure for Determination of Cleaning Efficacy by Weight.

The following procedure is used on each sample, with at least 2 replicates:

Step 1. The unsoiled item is weighed.

Step 2. Test soil is applied to the item.

Step 3. The soiled item is weighed. Items with more than ±10% deviation from mean mass were not used for testing but retained for % dried calculation. At least one soiled item was retained as a standard for % dried calculation.

Step 4. The cleaning experiment on the item was conducted. After cleaning, the item was allowed item to drain Step 5. Cleaned tubes and soiled standards were placed in a container containing dry silica in an oven at 56° C.

Step 6. The dried item was weighed after 1 day.

Step 7. The dried item was weighed after 3-5 days. Weighing was repeated until dried items attained a constant weight. (Drying time depends on the amount and distribution of soil in the item, the extent of moisture present and the air accessibility of the soil).

Step 8. The mass of soil removed by cleaning was obtained by the following formulae:

The mass removed by drying, per unit-mass of initial soil, from the drying control tubes was calculated by the following equation and their average determined:

$$\text{DryCal}=M_{init\ soil}/(M_{tube\ dry}-M_{tube\ unsoiled})$$

$$\text{Where: } M_{init\ soil}=(M_{tube\ soiled}-M_{tube\ unsoiled})$$

The percentage of soil removed is then calculated by the following equation:

$$M_{soil\ removed}=(M_{init\ soil}-((M_{tube\ dry}-M_{tube\ unsoiled})*\text{DryCal}_{ave}))/M_{init\ soil}$$

2.2 Procedure for Protein Staining of Lumens

The following procedure was used to stain protein residues for visual inspection:

Ingredients:

50% Methanol or EtOH

10% Glacial acetic acid 0.5% Coomassie G-250 (dehydrated)

40% H20

The above ingredients were combined and mixed well.

The stain was drawn into a syringe and filled into the tubes to be tested for residual protein. The tubes were then flushed with water until the solution colour exiting the tube was clear. Residual protein could be detected in the locations where the tube remained blue.

Uncontaminated tubing was subjected to the staining process and used as a control.

3. Cleaning by Paste

A number of 1 mm PTFE lumens were contaminated with protein as per the protein contamination procedure disclosed above.

A variety of commercial paste cleaners were forced through the lumen with the aid of an electronic caulking gun. After cleaning, the lumens were rinsed and the interiors stained with Coomassie blue to determine the presence of residual protein.

Flowable commercial cream cleaners demonstrated qualitative efficacy in reducing the presence of material stained blue relative to control staining. Cleaners that were too viscous or tacky were not sufficiently pumpable through small lumens at pressures within the range tolerable for endoscopes.

Further experiments were conducted on different pastes to determine the effect of crystal morphology, carrier fluid properties (such as viscosity) and solid fraction (ratio of solids to liquid phase) rheology of the paste/slurry and importantly, the cleaning action achievable in narrow, elongate lumens. In order to allow for proper comparison cleaning pastes, and apparatus designed to provide a continuous, measured flow of paste was constructed based around an electric caulking gun.

The pastes were prepared according to the table below. The ingredients were added to paddle blender bags and mixed in a paddle blender until a homogeneous consistency was achieved.

The paste is then pumped through 10 cm lengths of teflon tube, ID 4.25 mm, OD 5.1 mm. As the paste exits the tube it is collected in a beaker and the mass recorded.

This process was done twice for each paste; once to determine the removal of Soil 5B and again to determine the removal of fixed protein.

3.1 Soil Removal by Paste

After the passage of the paste through the 10 cm lengths of teflon tube, ID 4.25 mm, OD 5.1 mm, each tube was rinsed gently but thoroughly with water, with the aim of removing all the paste but not removing any further soil.

Once the cleaning process was carried out, each of the thus cleaned test lumens and the drying control lumens was dried over 48 hours at 56° C. and their weight recorded.

The mass removed by drying, per unit-mass of initial soil, from the drying control tubes is calculated by the following equation and their average determined:

$$\text{Dry}_{Cal}=M_{init\ soil}/(M_{tube\ dry}-M_{tube\ unsoiled})$$

The percentage of soil removed is then calculated by the following equation:

$$M_{soil\ removed}=(M_{init\ soil}-((M_{tube\ dry}-M_{tube\ unsoiled})*DryCal_{ave}))/M_{init\ soil}$$

Microscope photographs were taken of samples of the pastes to gain information on the crystal sizes and shapes.

The results are summarised in the table below:

| No | Paste | Pumping Voltage (V) | % Soil Removed (drying adjusted) | Protein Cleaning Comment | General Comments |
|---|---|---|---|---|---|
| 1 | Borax 58.94% Polyethylene Glycol (300 Mw) 32.85% Brij35 2.46% Water 5.75% | — | | Small spots of blue left | The paste was too thick to be pumped |
| 2 | Sodium Bicarbonate 69.33% Polyvinyl Alcohol (90-100k Mw) 1.53% Water 29.14% | 6 | 36.7 | Slight blue haze left | |
| 3 | Sodium Bicarbonate 64.33% Polyethylene Glycol 35.67% | 6 | 17.9 | Small spots of blue left | Could have been pumped at a faster rate |
| 4 | Sodium Bicarbonate 59.28% Glycerol 40.72% | 6 | 55.0 | Little to no effect | |
| 5 | Sodium Bicarbonate 63.91% Glycerol 36.09% | 15 | 65.9 | Almost no blue left | Almost too thick, nearly broke syringe |
| 6 | Sodium Bicarbonate 64.15% Xanthan Gum 0.47% Water 35.38% | 15 | 2.8 | Little to no effect | |
| 7 | Jiff | 15 | 20.9 | First 3rd Cleaned, no effect after | |
| 8 | Sodium Bicarbonate 64.27% Brij35 10.72% Water 25.01% | | | | Far too fluid to do any cleaning |
| 9 | Sodium Bicarbonate 58.84% Polyvinyl Alcohol (90-100k Mw) 2.06% Water 39.10% | | | | Far too fluid to do any cleaning |
| 10 | Aluminium Oxide 45% Polyethylene Glycol (300 Mw) 55% | | | | The paste was far too thick to be pumped |
| 11 | Calcium Carbonate 30.05% Glycerol 69.95% | 15 | 60.4 | No noticeable cleaning | |
| 12 | Calcium Carbonate 36.38% Glycerol 63.62% | 15 | 42.0 | No noticeable cleaning | |
| 13 | Calcium Carbonate 43.94% Polyethylene Glycol 56.06% | 15 | 18.2 | | |
| 14 | Calcium Carbonate 39.19% Polyethylene Glycol 60.81% | 15 | 14.6 | No noticeable cleaning | |
| 15 | Calcium Carbonate 47.36% Polyvinyl Alcohol (90-100k Mw) 2.63% Water 50.01% | 15 | 23.3 | No noticeable cleaning | |
| 16 | Calcium Carbonate 49.19% Polyvinyl Alcohol (90-100k Mw) 2.54% Water 48.27% | 12 | 21.3 | No noticeable cleaning | |
| 17 | Calcium Carbonate 45.36% Xanthan Gum 0.54% Water 54.10% | 15 | 19.3 | No noticeable cleaning | |
| 18 | Calcium Carbonate 49.78% Xanthan Gum 0.50% Water 49.72% | 15 | 42.2 | A slight cleaning effect | |
| 19 | Sodium Bicarbonate 40.59% Glycerol 59.41% | 15 | 50.9 | Almost perfect cleaning | Looked like decent cleaning for a relatively small paste volume |

-continued

| No | Paste | Pumping Voltage (V) | % Soil Removed (drying adjusted) | Protein Cleaning Comment | General Comments |
|---|---|---|---|---|---|
| 20 | Calcium Carbonate 48.25% Water 51.75% | 15 | 6.5 | No noticeable cleaning | Extremely thick paste, syringe plastic warped |

The carrier fluid can make a large difference in the behaviour of the cleaning suspension or paste. An example of this is Paste No. 3 and No. 5 both contained similar percentages of Sodium Bicarbonate, only in different carrier fluids and No. 3 was extremely fluid whereas No. 5 was extremely thick and had the greatest cleaning efficacy by soil mass removed.

Under all conditions Aluminium Oxide appeared to be unsuitable. This is believed to be due to the extremely small particle size.

Similarly, commercially available borax was also unsuitable due to clogging. This is believed to be due to the relatively large crystal size, which and may be addressed by milling the borax down to a smaller crystal size before mixing up the slurry.

The results raise the possibility that the exact mechanism of cleaning for soil is different from that for removing fixed protein. Paste No. 3 removed only 17.0% soil by mass, however, that same paste was very effective, on visual inspection, in removal of the protein Paste No. 11 produced the greatest result in terms of soil removal with 60% of the soil cleaned.

While Paste No. 19 removed only 50% of the soil it had a greater efficacy per gram of paste used (2.03% per gram)

Paste No. 19 also proved much better at cleaning fixed protein than Paste No. 11

Sodium Bicarbonate in Glycerol paste was particularly useful.

The differences between Paste No. 1 and Paste No. 19 are interesting as they have the same carrier fluid but different solid particles and while they both clean soiled tubes similarly, their efficacy when cleaning fixed protein is very different.

3.2. Paste Cleaning-Initial Volume Testing

Initial testing has shown that a small volume of paste can clean a significant amount of soil 5B and also that using a larger volume increases the efficacy, with the potential to clean the tube entirely.

ID 4.25 mm, OD 5.1 mm ID PTFE tubing was contaminated with soil 5B as described above. Two specific pastes were prepared:

1) Sodium bicarbonate (120.24 g)+Glycerol (80.86 g)=59.79% sodium bicarbonate % w/w.
2) Sodium Bicarbonate (128.56 g)+PEG 300 (71.93 g)=64.12% sodium bicarbonate % w/w.

These were pumped through the tubing at 15V. The amount of paste used was recorded.

The 59.79% sodium bicarbonate in glycerol created a significant amount of back pressure with this paste when a larger volume of was used. The soil initially appeared to be removed well, however as more paste went through the tube, less soil was removed, and the final portion of pumped paste did not appear to remove any soil additional soil.

64.12% sodium bicarbonate in PEG was very smooth running. The initial portion of paste cleaned well but as with the paste above, the cleaning efficacy tailed off as more paste was used.

Thus, simply increasing a quantity of cleaning paste through a lumen is not sufficient to ensure that a desired cleaning outcome can be obtained.

3.3 Paste Test—Detailed Solids Removal

A detailed examination of the most suitable pastes was conducted.

| Paste | Paste used (g) | Wet soil (g) | Wet soil left (g) | Wet soil left% | Ave Wet soil left % |
|---|---|---|---|---|---|
| ⅓ Sodium Benzoate ⅓ Water ⅓ Sodium Bicarb | 29.1000 | 0.32 | 0.0017 | 2.10 | 0.51 |
| ⅓ Sodium Benzoate ⅓ Water ⅓ Sodium Bicarb | 31.5100 | 2.56 | −0.0001 | −0.14 | |
| ⅓ Sodium Benzoate ⅓ Water ⅓ Sodium Bicarb | 37.5900 | 4.92 | −0.0004 | −0.42 | |
| 50% Sodium Benzoate 50% Water | 32.2200 | 2.78 | 0.0035 | 4.41 | 2.37 |
| 50% Sodium Benzoate 50% Water | 19.0500 | 4.67 | 0.0027 | 3.26 | |
| 50% Sodium Benzoate 50% Water | 22.6200 | 6.41 | −0.0005 | −0.55 | |
| 68% Sodium Bicarb in Propylene Glycol | 70.2700 | 9.49 | 0.0028 | 3.85 | 4.71 |
| 68% Sodium Bicarb in Propylene Glycol | 75.7700 | 0.32 | 0.0035 | 4.34 | |
| 68% Sodium Bicarb in Propylene Glycol | 63.8900 | 13.12 | 0.0042 | 5.94 | |

-continued

| Paste | Paste used (g) | Wet soil (g) | Wet soil left (g) | Wet soil left% | Ave Wet soil left % |
|---|---|---|---|---|---|
| Water Flush | 51.6600 | 8.37 | 0.0184 | 24.89 | 24.89 |
| Water Flush | 51.6600 | 10.23 | 0.0112 | 15.54 | 15.54 |
| Water Flush | 51.6600 | 14.48 | 0.0197 | 21.38 | 21.38 |

The pastes were all significantly more effective than a water flush at removing contaminants.

3.4 Paste Test Results—Protein Removal

| | Paste used | Image |
|---|---|---|
| 68% Sodium Bicarb in Propylene Glycol | 73.9200 | excellent |
| 68% Sodium Bicarb in Propylene Glycol | 77.2100 | excellent |
| ⅓ Sodium Benzoate ⅓ Water ⅓ Sodium Bicarb | 23.8400 | excellent |
| ⅓ Sodium Benzoate ⅓ Water ⅓ Sodium Bicarb | 34.3600 | good |
| 50% Sodium Benzoate 50% Water | 27.1700 | good |
| 50% Sodium Benzoate 50% Water | 21.3000 | good |

The pastes used in the above table were found to be suitable for the removal of residual protein.

In general pastes comprising almost equal quantities (w/w) of sodium benzoate, sodium bicarbonate and water were found to give good cleaning. That is, a range of pastes comprising 25-45% sodium benzoate, 25-45% sodium bicarbonate and 25-45% water were all suitable for cleaning endoscope lumens. The amount of each component used could be independently varied, provided all three quantities stayed within the stated quantities.

One particularly beneficial formulation comprises sodium benzoate, sodium bicarbonate and water in the respective ratios 27:35:38 w/w.

In these preferred formulations, the sodium bicarbonate particles used all had a particle size below 0.15 mm. A range of particle sizes of sodium benzoate were tested between 1 mm and 0.15 mm. In general, the smaller particles appeared to provide better results. However, it was observed that if these three component (bicarb, benzoate and water) mixtures were allowed to stand for some time between mixing and use, the differences in sodium benzoate particle size became less pronounced.

3.5 Visual Inspection of Soil Removal.

Endoscope lumens are of extremely long length in relation to their diameter, which is a factor contributing to the difficulty in their cleaning. In order to better model the cleaning processes in such elongate systems, the cleaning processes were carried out in an endoscope that was specially constructed to have a semi-transparent Teflon tube as a lumen configured to connect with all the internal passageways and having all the necessary external connections and ports present in a commercial endoscope, but without the external casing. This enabled the cleaning of the lumen to be visually examined. The lumen of the uncased endoscope was approximately 1700 mm in length and 4.0 mm inside diameter.

The visible inner workings of the endoscope were particularly useful in examining the efficacy of the suspension methods of the present invention, and in particular, the paste method. Because the paste is white, it provides a clear visual contrast with the dark red or brown soil present in the lumen. The white paste displaces the red soil from the interior lumen, changing the exterior appearance of the Teflon tube as it does so. This enables the progress of the cleaning along the tube to be monitored readily. When the soil is fully removed, the tube is white in appearance and can be compared against a control, which contains the paste in an unsoiled lumen. This can be monitored visually, although colourimetric measurements can be made on the paste exiting the lumen to determine whether the paste contains any removed soil. In such a case, the paste continues to be pumped through the lumen until no further discolouration due to contaminants is detected. The paste was passed through the lumen at a pressure of 35 psi for around 4 to 5 minutes for a total volume of around 60-100 ml of paste, which is a volume similar to the total volume of the lumen.

The pastes of the present invention, in particular, the pastes comprising 25-45% sodium benzoate, 25-45% sodium bicarbonate and 25-45% water, were all highly effective in removing the various artificial soils from the interior of the lumen wall as determined by visual inspection.

After the required volume of paste had been applied, water could be passed through the lumen to remove the paste. The water can be used immediately after the paste, and in direct contact with the paste, to continue the flow through the lumen. The wash phase typically required around 30-60 seconds to remove all of the paste and return the lumen to a useable condition.

The invention claimed is:

1. A method of building a stable biofilm in a lumen comprising:

depositing a fixed layer of protein on the lumen, comprising a first set of ordered steps of:

(a) applying a protein-containing, biological fluid solution to the lumen; and (b) fixing protein from the solution with a glutaraldehyde solution to deposit a fixed layer of protein to the lumen; and applying an inoculated growth medium comprising a bacterial strain capable of forming a biofilm onto the fixed layer of protein, wherein the application of the growth medium gives rise to a stable biofilm.

2. The method of claim 1, wherein the first set of ordered steps (a) and (b) is repeated a plurality of times.

3. The method of claim 2, wherein the bacterial strain comprises a *Pseudomonas aeruginosa* strain.

4. The method of claim 1, wherein the glutaraldehyde solution ranges between approximately 1-3% glutaraldehyde.

5. The method of claim 4, wherein the glutaraldehyde solution comprises approximately 1% glutaraldehyde.

6. The method of building a stable biofilm in a lumen of claim 1, wherein the application of the growth medium to a fixed layer of protein on a lumen comprises a second set of ordered steps of:

(c) pumping an inoculated growth medium comprising a *Pseudomonas aeruginosa* strain through the lumen at flow rate of approximately 5 L/min at least 48 hours;

(d) stopping the pump and allowing the medium to drain from the lumen;

(e) replacing the growth medium with fresh growth medium; and (f) repeating the second set of ordered steps (c)-(e) once, and then repeating the second set of ordered steps (c)-(d) once.

7. The method of claim 6, wherein in the repetition of step (e), the growth medium is pumped for approximately 72 hours.

8. The method of claim 6, wherein the growth medium is continually stirred and recirculated from (i) a flask maintained in a water bath at approximately 30 degrees C., (ii) through the lumen, and (iii) to the flask again.

9. The method of claim 6, wherein the *Pseudomonas aeruginosa* strain is ATCC15442.

10. The method of claim 6, wherein the any one or more of:

(a) the volume of the protein-containing biological fluid solution pumped through the lumen;

(b) the concentration of the protein-containing biological fluid solution;

(c) the volume of the glutaraldehyde solution pumped through the lumen;

(d) the concentration of the glutaraldehyde solution;

(e) the volume used to wash the lumen;

(f) the flow rate of the inoculated growth medium; and (g) the number of hours the growth medium is pumped through the lumen for each new batch of growth medium is or are varied by up to 15% to achieve the deposition of an equally stable biofilm.

11. The method of claim 6, wherein the concentration of the *Pseudomonas aeruginosa* strain added to create the growth medium is determined by percent transmission using spectrophotometry at approximately 580 nm.

12. The method of claim 6, wherein the lumen containing the stable biofilm is stored at approximately −4 degrees C.

13. The method of claim 1, wherein the stable biofilm is deposited for testing medical device cleaning processes.

14. The method of claim 1, wherein the lumen is sterilized prior to depositing the fixed layer of protein.

15. The method of claim 1, wherein the any one or more of the following is or are varied by up to 15% to achieve the deposition of an equally stable biofilm:

(a) the volume of the protein-containing biological fluid solution pumped through the lumen;

(b) the concentration of the protein-containing biological fluid solution;

(c) the volume of the glutaraldehyde solution pumped through the lumen;

(d) the concentration of the glutaraldehyde solution;

(e) the volume used to wash the lumen;

(f) the flow rate of the inoculated growth medium; and (g) the number of hours the growth medium is pumped through the lumen for each new batch of growth medium.

16. A method of depositing a fixed layer of protein on a lumen comprises the ordered steps of:

(a) pumping a volume of a protein-containing biological fluid solution equal to twice a volume held by a completely filled lumen through the lumen, and waiting at least 20 minutes;

(b) pumping a volume of the glutaraldehyde solution equal to twice the volume held by the completely filled lumen through the lumen, and waiting at least 10 minutes;

(c) repeating the ordered steps (a) and (b) at least five times to deposit a fixed layer of protein on the lumen; and (d) washing the lumen with a volume of water equal to up to ten times the volume held by the completely filled lumen.

17. The method of claim 16, wherein the protein-containing biological fluid solution comprises a solution of serum from animal blood.

18. The method of claim 17, wherein the solution comprises approximately 1% horse serum.

19. The method of claim 16, wherein the glutaraldehyde solution comprises approximately 1% glutaraldehyde.

20. The method of claim 16, wherein the any one or more of the following is or are varied by up to 15% to achieve the deposition of an equally stable biofilm:

(a) the volume of the protein-containing biological fluid solution pumped through the lumen;

(b) the concentration of the protein-containing biological fluid solution;

(c) the volume of the glutaraldehyde solution pumped through the lumen;

(d) the concentration of the glutaraldehyde solution;

(e) the volume used to wash the lumen;

(f) the flow rate of the protein-containing biological fluid solution; and (g) the number of hours the protein-containing biological fluid solution is pumped through the lumen for each new batch of growth medium.

21. A method of adhering a stable biofilm to a lumen of a medical device, comprising ordered steps of:

depositing a fixed layer of protein on the lumen, comprising the ordered steps of:

(a) pumping a solution comprising animal serum through the lumen; and (b) fixing the protein from biological solution to the lumen by pumping a glutaraldehyde solution through the lumen;

(c) repeating ordered steps (a) and (b) at least two times; and preparing an inoculated growth medium comprising a bacterial strain capable of forming a biofilm on the fixed layer of protein;

adhering a layer of biofilm on the fixed layer of protein on the lumen, comprising the ordered steps of:

(d) recirculating the inoculated growth medium from the flask through the lumen and back, and allowing the medium to drain from the lumen;

(e) preparing a new batch of growth medium and repeating step (d);

(f) repeating step (e), wherein the layer of protein acts as a scaffold to which the biofilm is adhered and rendered stable for testing of medical device cleaning protocols.

22. The method of claim 21, wherein the bacterial strain comprises *Pseudomonas aeruginosa*.

23. The method of claim 22, wherein the *Pseudomonas aeruginosa* strain comprises ATCC15442.

24. The method of claim 22, wherein the number of hours during which the medium is pumped through the lumen varies by up to 15% to achieve the adherence of a stable biofilm to a lumen.

25. The method of claim 24, wherein recirculating the growth medium comprises recirculating the growth medium at a rate of no more than approximately 5 L/min.

26. The method of claim 21, wherein the number of hours during which the medium is pumped through the lumen varies by up to 15% to achieve the adherence of a stable biofilm to a lumen.

27. The method of claim 21, wherein the growth medium is recirculated in (d) through the lumen for at least about 48 hours.

28. The method of claim 21, wherein the growth medium is recirculated in (e) through the lumen at least about 72 hours.

29. The method of claim 21, wherein the stable biofilm is deposited for testing medical device cleaning processes.

30. The method of claim 21, wherein the serum comprises approximately 0.5 to approximately 4% horse serum.

31. The method of claim 21, wherein the lumen is sterilized prior to depositing the fixed layer of protein.

32. The method of claim 21, wherein the growth medium is pumped through the lumen at a flow rate selected from the group consisting of less than 8 L/min, less than 7 L/min, less than 6 L/min and less than 5 L/min.

33. The method of claim 1, wherein the protein-containing biological fluid solution comprises protein from serum.

* * * * *